US011464583B2

(12) United States Patent
Sano et al.

(10) Patent No.: US 11,464,583 B2
(45) Date of Patent: Oct. 11, 2022

(54) SURGERY SUPPORT APPARATUS AND SURGICAL NAVIGATION SYSTEM

(71) Applicant: Hitachi, Ltd., Tokyo (JP)

(72) Inventors: Yuko Sano, Tokyo (JP); Yusuke Seki, Tokyo (JP); Nobutaka Abe, Tokyo (JP); Takafumi Shimamoto, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 279 days.

(21) Appl. No.: 16/881,127

(22) Filed: May 22, 2020

(65) Prior Publication Data

US 2021/0085401 A1 Mar. 25, 2021

(30) Foreign Application Priority Data

Sep. 25, 2019 (JP) .............................. JP2019-174600

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 90/37* (2016.02); *G06T 7/0012* (2013.01);
(Continued)

(58) Field of Classification Search
CPC ......... A61B 34/10; A61B 34/20; A61B 34/25; A61B 2034/107; A61B 2034/108;
(Continued)

(56) References Cited

U.S. PATENT DOCUMENTS

2017/0035517 A1* 2/2017 Geri .................... A61B 34/20
2017/0046826 A1* 2/2017 Konen ............... G01R 33/4835
(Continued)

FOREIGN PATENT DOCUMENTS

JP 2019500110 A 1/2019

OTHER PUBLICATIONS

Coffey et al. "An evaluative tool for preoperative planning of brain tumor resection." Medical Imaging 2010: Visualization, Image-Guided Procedures, and Modeling. vol. 7625. International Society for Optics and Photonics, 2010. (Year: 2010).*
(Continued)

*Primary Examiner* — Katrina R Fujita
(74) *Attorney, Agent, or Firm* — Mattingly & Malur, PC

(57) ABSTRACT

The accuracy of an intervention site in surgery is predicted and the predicted intervention site is presented to a surgeon. A surgery support apparatus includes a prediction data generation unit that generates prediction data predicting an intervention site based on data before an intervention using an artificial intelligence algorithm. The artificial intelligence algorithm is an artificial intelligence algorithm learning an intervention site by analyzing data before the intervention and intervention site data for an object, and outputs coordinates, a region, or a shape of one point of the intervention site as prediction data. Data before the intervention used for learning of the artificial intelligence algorithm and input data input to the artificial intelligence algorithm to generate prediction data correspond to image data, a segment image, a feature point, etc. The prediction data is displayed on a display apparatus together with an image of a patient acquired in advance.

14 Claims, 17 Drawing Sheets

(51) Int. Cl.
  *A61B 90/00* (2016.01)
  *G06T 7/00* (2017.01)
  *G06T 7/11* (2017.01)
(52) U.S. Cl.
  CPC .......... *G06T 7/11* (2017.01); *A61B 2034/107* (2016.02); *A61B 2034/2059* (2016.02); *G06T 2207/20021* (2013.01); *G06T 2207/20084* (2013.01); *G06T 2207/30016* (2013.01); *G06T 2207/30096* (2013.01)
(58) Field of Classification Search
  CPC .... A61B 2034/2055; A61B 2034/2059; A61B 2034/2065; A61B 90/37; G06T 7/0012; G06T 7/11; G06T 7/70; G06T 2207/10072; G06T 2207/20021; G06T 2207/20084; G06T 2207/30016; G06T 2207/30096
  See application file for complete search history.

(56) References Cited

U.S. PATENT DOCUMENTS

| | | | |
|---|---|---|---|
| 2017/0348056 A1* | 12/2017 | Steinle | A61B 90/37 |
| 2018/0217734 A1* | 8/2018 | Koenig | A61B 34/25 |
| 2018/0365824 A1 | 12/2018 | Yuh et al. | |
| 2020/0357120 A1* | 11/2020 | Kang | A61B 5/055 |
| 2021/0015560 A1* | 1/2021 | Boddington | A61B 90/361 |
| 2021/0204914 A1* | 7/2021 | Meral | A61B 8/0808 |
| 2021/0401501 A1* | 12/2021 | Avisar | G16H 50/50 |

OTHER PUBLICATIONS

Tonutti et al. "A machine learning approach for real-time modelling of tissue deformation in image-guided neurosurgery." Artificial intelligence in medicine 80 (2017): 39-47. (Year: 2017).*

* cited by examiner

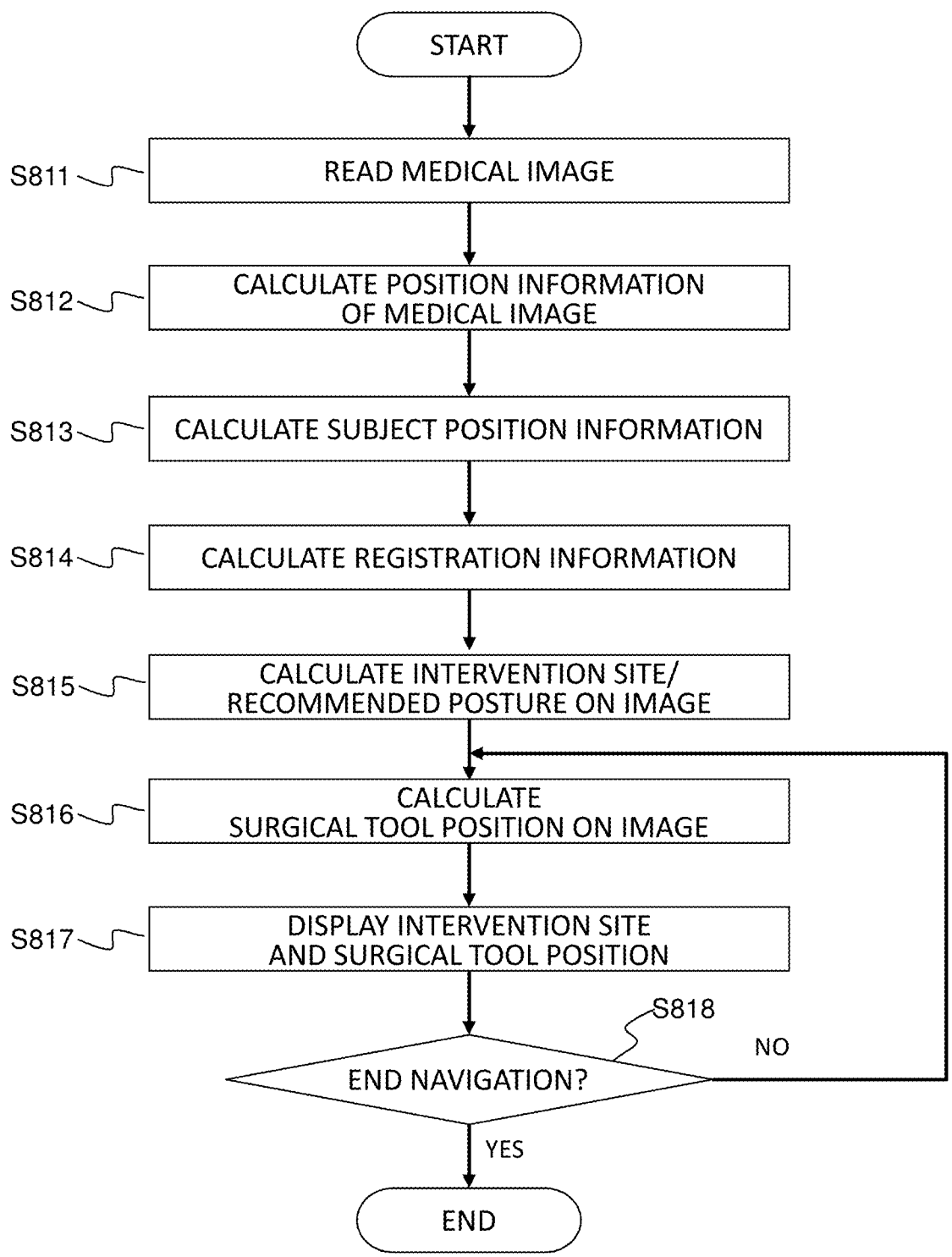

BEFORE CRANIOTOMY

AFTER CRANIOTOMY

SURGERY SUPPORT APPARATUS AND SURGICAL NAVIGATION SYSTEM

INCORPORATION BY REFERENCE

The present application claims priority from Japanese patent application JP-2019-174600 filed on Sep. 25, 2019, the content of which is hereby incorporated by reference into this application.

BACKGROUND OF THE INVENTION

Field of the Invention

The present invention relates to a surgery support apparatus and a surgical navigation system that support a surgeon using a medical image during surgery.

Description of the Related Art

There has been known a surgical navigation system that supports a surgeon so that surgery can be safely performed by integrating treatment plan data created before surgery with data acquired during surgery to guide a position and posture of a surgical tool, etc.

More specifically, for example, the surgical navigation system is a system that presents a position of a surgical tool to the surgeon to support surgery by superimposing and displaying position information in a real space of various medical devices such as the surgical tool detected using a sensor such as a position measuring apparatus on a medical image acquired before surgery by a medical image capturing apparatus such as an MRI.

One of problems to be solved by the surgical navigation system is to present an appropriate intervention site to the surgeon. The intervention site is a body surface portion at the time of incising a body surface of a subject, that is, a patient using a surgical tool to perform treatment on a tissue or an organ inside a body corresponding to a subject of surgery, and it is necessary to set an appropriate position and size according to a position of a site to be treated. Conventionally, when a surgeon intervenes in a body of a patient during surgery, an intervention site has been determined based on an experience of the surgeon with reference to a medical image. However, when the surgeon has little experience, an appropriate intervention site matching the purpose of the surgery may not be properly determined, and the position is shifted or a range is excessively small. In this case, correction such as expansion of the intervention site is performed again after the intervention, and a physical load on the patient due to the excessive surgery time increases.

In particular, in surgery such as brain surgery involving resection of a skull and craniotomy such as removal of a brain tumor, it is necessary to comprehensively determine a resection site (intervention position) based on various factors such as a size of the tumor, a distance to the tumor, and a location of a brain area where damage needs to be avoided, and it is necessary to appropriately set a body position of the patient according to the resection site. An unskilled surgeon may not be able to properly determine the resection site and may require additional resection of the skull after resection. However, no technology has been proposed to address such a problem.

Meanwhile, in recent years, a technology for improving accuracy of a medical image using an artificial intelligence algorithm such as deep learning has been developed. For example, JP-T-2019-500110 (the term "JP-T" as used herein means a published Japanese translation of a PCT patent application) discloses a technology for determining intracranial bleeding, etc. from a medical image.

The technology using the artificial intelligence algorithm disclosed in JP-T-2019-500110 indirectly contributes to surgery support by, for example, improving the accuracy of determining the surgical site. However, the technology merely improves image accuracy, and does not provide support information combined with a surgical navigation technology. In contrast, the present applicant proposes a technology for improving accuracy of a surgical tool position presented by surgical navigation by predicting a position of a target organ after an intervention using an artificial intelligence algorithm learning images before and after the intervention as teacher data. In this technology, it is possible to solve a problem that the target organ is deformed by an intervention of the surgeon, for example, incision, and accuracy of a surgical tool position presentation function by surgical navigation is reduced, for example, a problem caused by a so-called "brain shift" in which a shape and a position of the brain are changed by craniotomy in brain surgery.

However, changes in the shape and position of the organ after the intervention differ depending on the position of the intervention and the body position of the patient. However, this technology does not provide support information for the intervention position thereof. In some cases, the intervention position needs to be flexibly changed in consideration of a condition of the patient (for example, a type of body position to be taken), etc. There is a possibility that a sufficient surgery support function may not be obtained only by the above-mentioned artificial intelligence algorithm. In addition, to create an artificial intelligence algorithm that can predict the shape and position change of the organ after the intervention in consideration of the intervention position and the patient body position, a huge amount of teacher data is required.

SUMMARY OF THE INVENTION

Therefore, an object of the invention is to provide a technology for predicting an appropriate intervention site for surgery in a surgical navigation system.

To solve the above-mentioned problem, a surgery support technology of the invention creates an artificial intelligence algorithm learning an intervention site by analyzing data before an intervention and intervention site data for an object, and predicts and presents an intervention site based on data before the intervention using the learned artificial intelligence algorithm.

Specifically, a surgery support apparatus of the invention is a surgery support apparatus for supporting an intervention in an object in a living body by displaying an image, characterized by including a prediction data generation unit that uses a learned artificial intelligence algorithm learned using image data including the object before the intervention or data obtained by processing the image data and information related to an intervention position on a surface of the living body to predict an intervention position in the living body to be treated, and outputs prediction data.

In addition, the invention provides a surgical navigation system including the surgery support apparatus. The surgical navigation system includes the surgery support apparatus, a display apparatus that displays a medical image, and a position measuring apparatus that measures a position of a living body to be treated and a position of a surgical tool. The surgery support apparatus causes the display apparatus to display information related to an intervention position output by the prediction data generation unit and a position of the surgical tool measured by the position measuring apparatus.

According to the invention, accuracy of an intervention site can be improved by predicting an appropriate intervention site with respect to a surgery subject, and presenting the predicted intervention site to a surgeon. As a result, a physical load on a patient can be reduced.

Figure 10A:
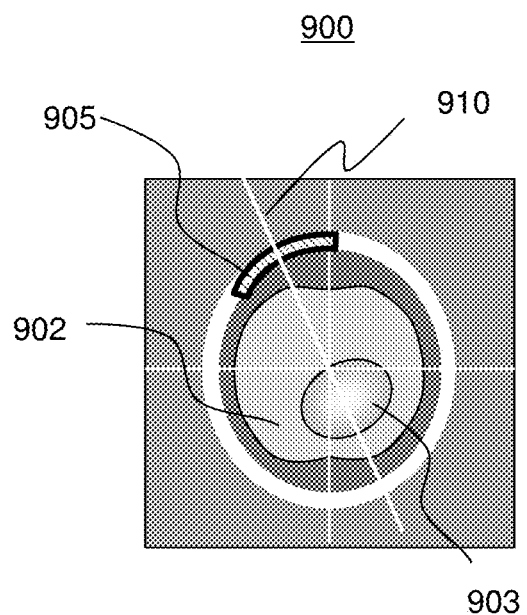
Figure 10B:
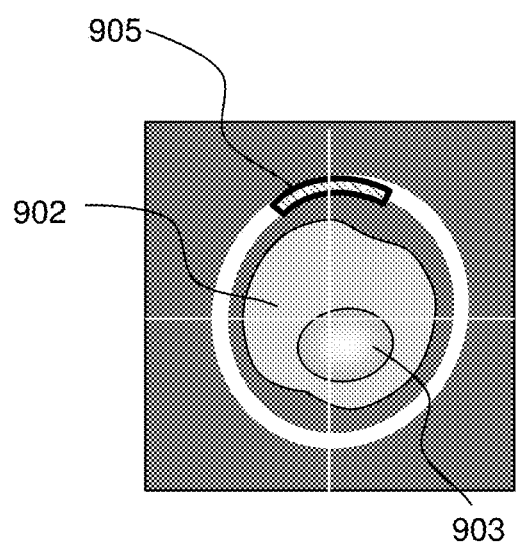
Figure 12:
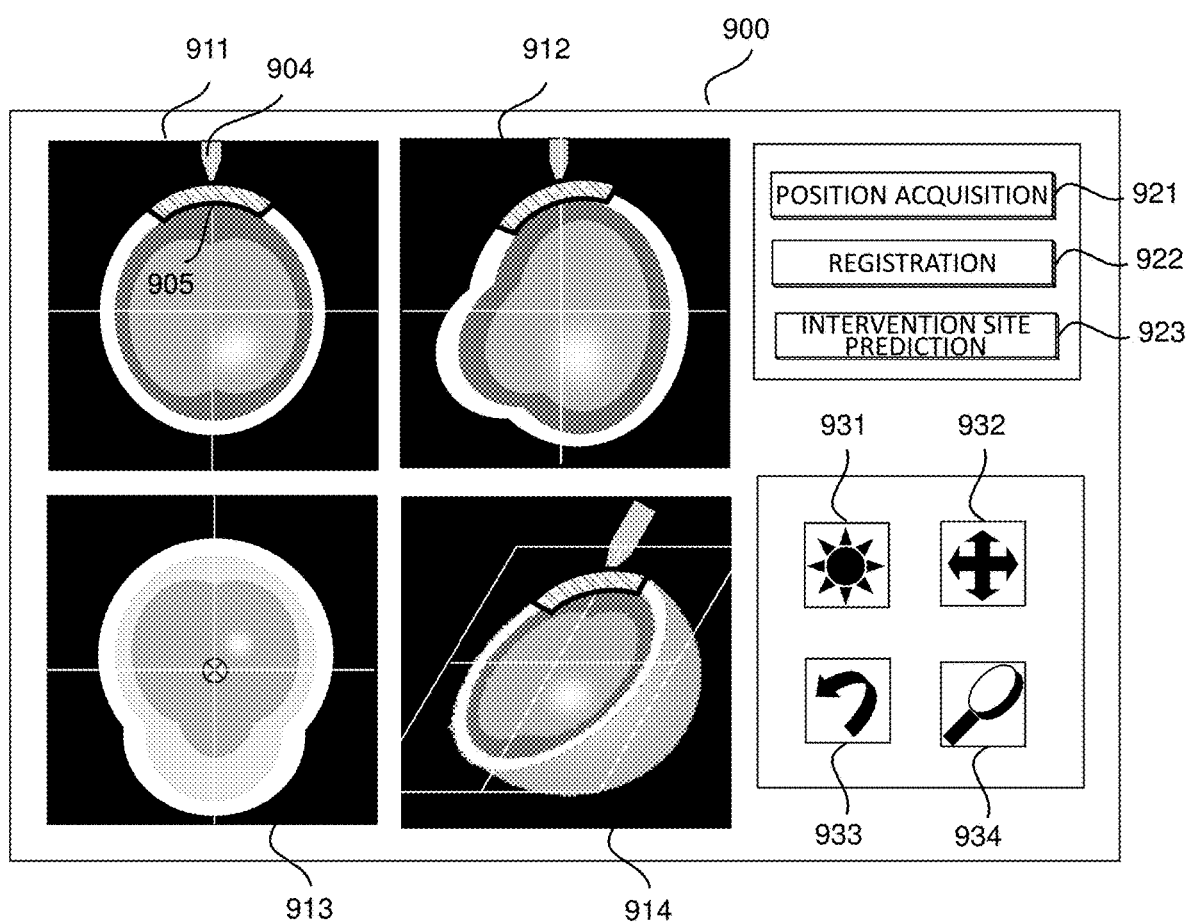
Figure 13A:
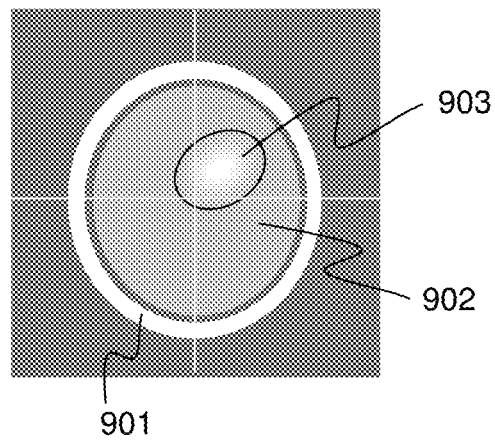
Figure 13B:
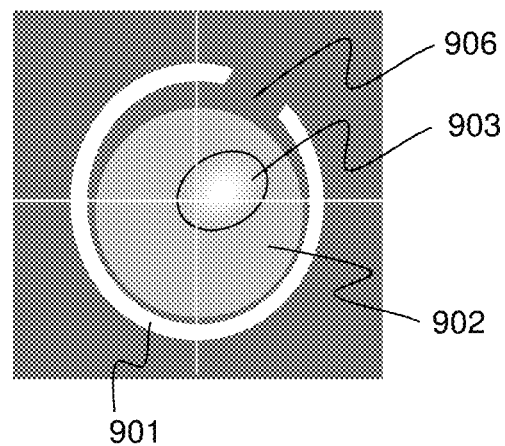
Figure 14:
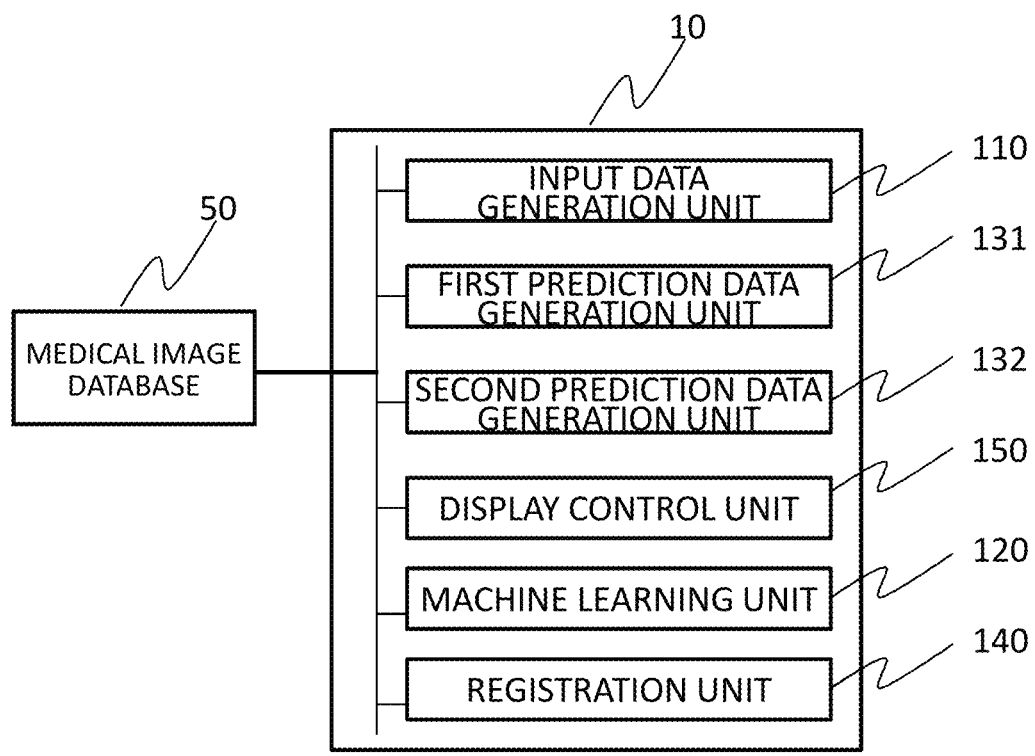
Figure 15:
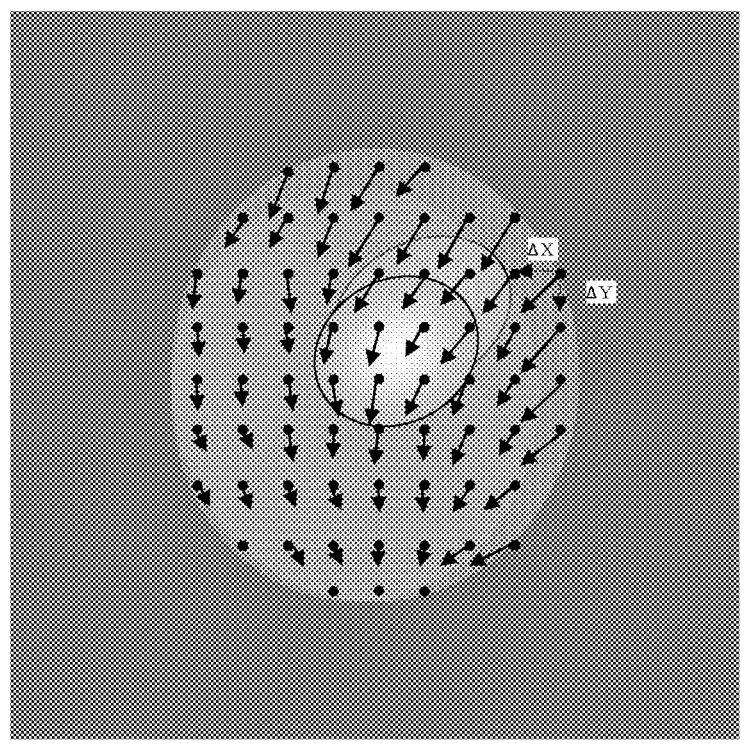
Figure 16:
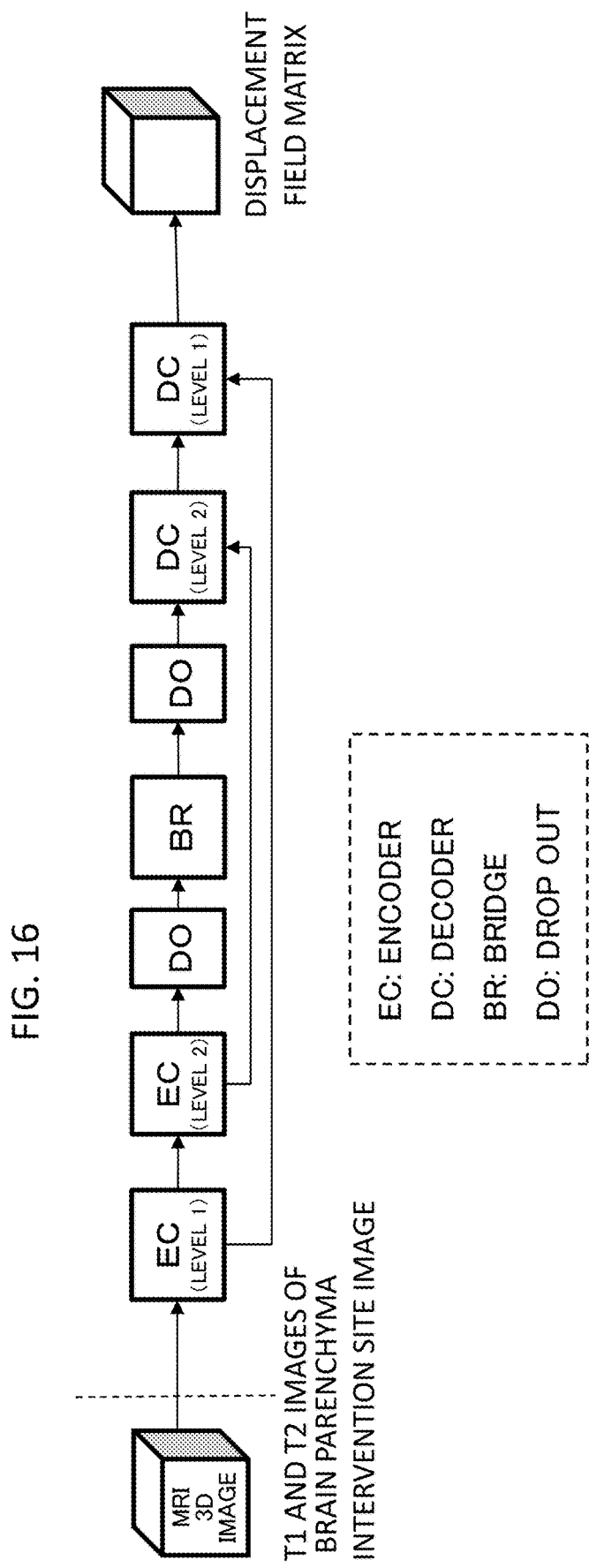
Figure 17:
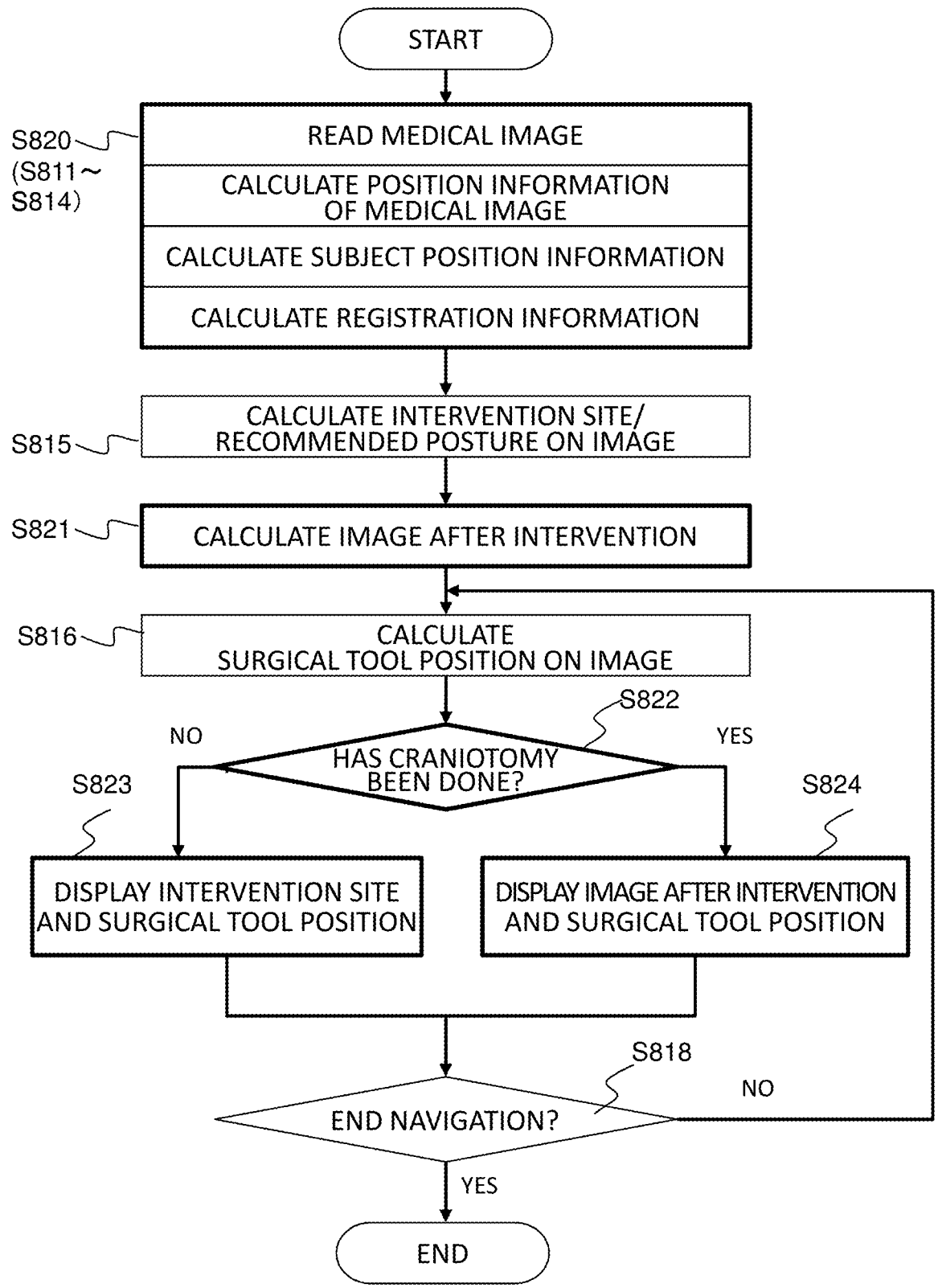

Each of FIGS. 10A and 10B is a diagram illustrating another example of the display screen displayed on the display apparatus in the surgery support apparatus of the first embodiment;

FIG. 11 is a flowchart describing a process of the surgical navigation system according to the first embodiment;

FIG. 12 is a diagram illustrating an example of a display screen displayed on the display apparatus in the surgical navigation system according to the first embodiment;

FIGS. 13A and 13B are reference diagrams of a tomographic image of a brain for describing a brain shift, in which FIG. 13A illustrates a state before craniotomy, and FIG. 13B illustrates a state after craniotomy;

FIG. 14 is a block diagram of a configuration of a central processing device of a surgery support apparatus of a second embodiment;

FIG. 15 is a diagram illustrating an example of output data of an artificial intelligence algorithm of the surgery support apparatus of the second embodiment;

FIG. 16 is a diagram illustrating an example of an artificial intelligence algorithm applied to the surgery support apparatus of the second embodiment; and FIG. 17 is a flowchart describing a process of a surgical navigation system according to the second embodiment.

DETAILED DESCRIPTION OF THE INVENTION

Embodiments of a surgical navigation system according to the invention will be described with reference to the drawings.

Figure 1:
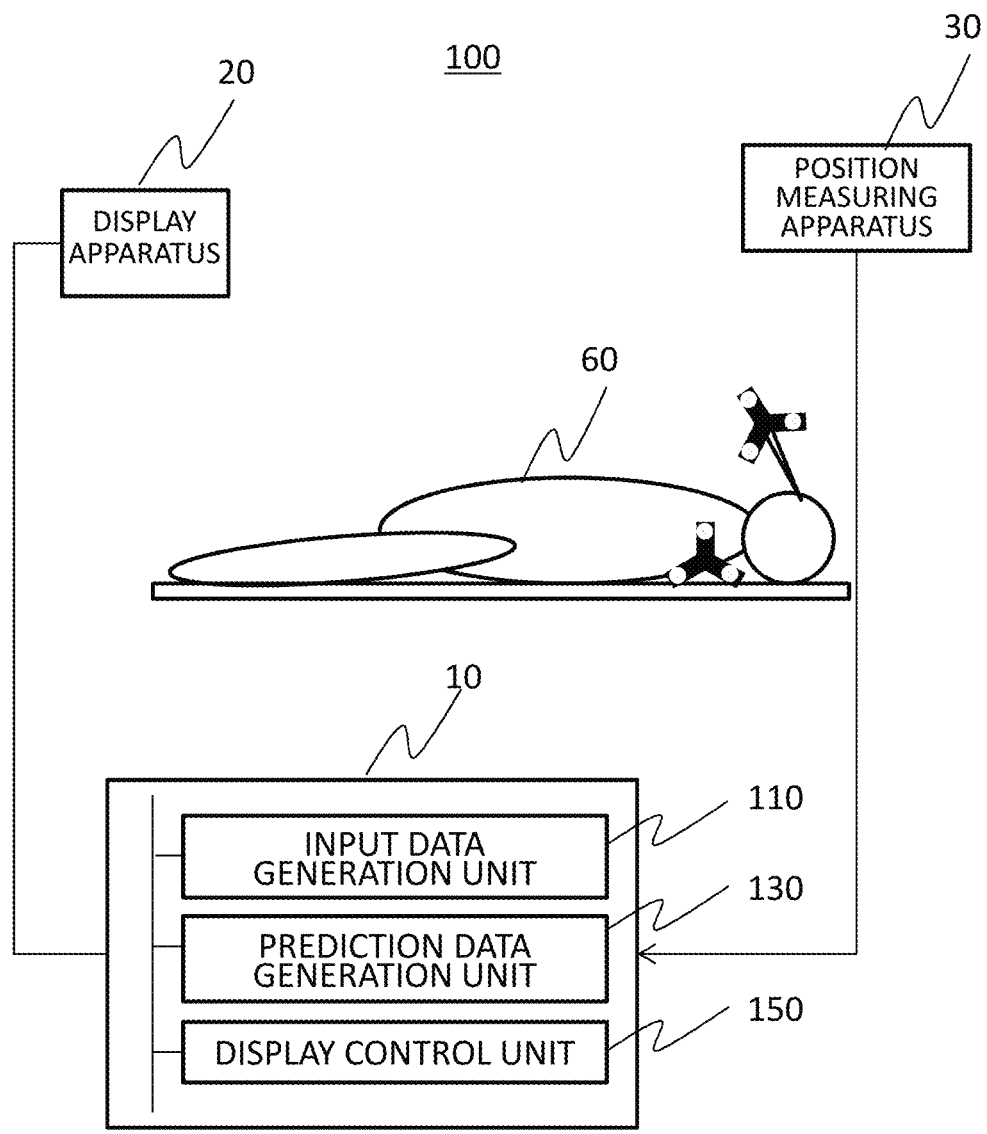
FIG. 1 is a block diagram illustrating a schematic configuration of a surgical navigation system according to an embodiment of the invention.

As illustrated in FIG. 1, a surgical navigation system 100 includes a surgery support apparatus 10 that generates information (support information) necessary for surgery support, an output unit that presents the information generated by the surgery support apparatus 10 to a surgeon, for example, a display apparatus 20, and a position measuring apparatus 30 that measures a position of a patient or a surgical tool placed in an operating room.

The surgery support apparatus 10 is an apparatus that supports the surgeon by superimposing position information of the surgical tool, etc. on a desired medical image to present the position information in real time. Specifically, information related to a position of the patient (target site) or the surgical tool is acquired from the position measuring apparatus 30 and displayed on the display apparatus 20 together with a preoperative image. Furthermore, in the present embodiment, support information including information related to an appropriate intervention position is generated based on input data generated from image data (preoperative image data) of a target site acquired prior to an intervention in the patient, and displayed on the display apparatus 20 together with the position information of the surgical tool.

As the preoperative image, an image of the patient acquired by a medical imaging apparatus such as an MRI apparatus or a CT apparatus can be stored in a storage device in the surgery support apparatus 10 or an external storage device, and read and used by the surgery support apparatus 10 during creating of input data or during displaying on the display apparatus 20 as support information.

The input data generated by the surgery support apparatus 10 may correspond to the preoperative image, or correspond to a segmentation image obtained by extracting a region having a predetermined feature (hereinafter, a feature region) from the preoperative image, feature point data obtained by extracting a feature of a tissue or a site, etc. In addition, the support information output by the surgery support apparatus 10 may include information indicating a change after the intervention such as a brain shift in addition to the information related to the intervention position. The information related to the intervention position includes a position or region to be intervened, a size, an inclination of a line connecting the intervention position and the target site, a recommended body position of the patient estimated from the inclination, etc.

For example, the surgery support apparatus 10 uses a plurality of sets including the same type of input data as the above-described input data and data (teacher data) related to the intervention position corresponding to an output of the surgery support apparatus 10 to output the above-described support information using a pre-learned artificial intelligence algorithm (hereinafter, abbreviated as an AI algorithm) finishing learning. Such an AI algorithm is created in the surgery support apparatus 10 or another apparatus, and stored in the storage device in the surgery support apparatus 10 or an external storage device. A method of creating the AI algorithm will be described later in detail.

To implement the above-described functions, the surgery support apparatus 10 may include an input data generation unit 110 that generates input data from a preoperative image, a prediction data generation unit 130 that generates information related to an intervention position from the input data using an AI algorithm, and a display control unit 150 for causing the display apparatus 20 to display an output of the prediction data generation unit 130 and an output from the position measuring apparatus 30. These functions can be implemented on a general-purpose or dedicated computer including a processing apparatus such as a central processing unit (CPU), a graphics processing unit (GPU), or a combination thereof. A program that functions as the input data generation unit 110, the prediction data generation unit 130, or the display control unit 150 is implemented as software by reading the program into a memory of the computer and executing the program. However, some or all of the functions executed by the processing apparatus may be implemented by hardware such as an application specific integrated circuit (ASIC) or a field-programmable gate array (FPGA). In addition, depending on the embodiment, some functions may be omitted.

The position measuring apparatus 30 detects a position of a marker placed in the vicinity of a patient corresponding to a surgery target in the operating room or a marker fixed to the surgical tool, and acquires a three-dimensional (3D) position of the patient or the surgical tool in a real space coordinate system. For the detection of the marker, a known position detector such as a magnetic detector or an infrared detector can be employed. The position of the target site or the surgical tool in the real space coordinate system is subjected to coordinate transformation into a position of coordinates of DICOM data (coordinates in an image space), and is superimposed on the preoperative image and displayed on the display apparatus 20. For example, a registration unit (coordinate transformation unit) may be provided in a central processing device 11, and coordinate transformation may be implemented therein. A known surgical navigation scheme may be used as a registration scheme.

According to the surgical navigation system of the present embodiment, it is possible to present an optimal intervention position for a surgery target to the surgeon by preparing an AI algorithm learning to output an appropriate intervention position with respect to input data using a plurality of data sets, generating the same type of input data as input data of the AI algorithm for the surgery target, and inputting the generated input data to the learned AI algorithm. In this way, an improper intervention can be prevented, for example, to cause the patient to take a proper body position or to assist in surgery having minimal invasion in a shortest path.

Based on the embodiment of the basic configuration of the surgical navigation system described above, a specific embodiment of the invention will be described below, taking a case where the surgery is a brain surgery involving craniotomy as an example. Note that, in the following embodiments, the same elements as those included in FIG. 1 are denoted by the same reference numerals, and redundant description will be omitted.

First Embodiment

A surgical navigation system according to the present embodiment is an embodiment in which the surgery support apparatus 10 is constructed on a computer including a central processing device, and the input data generation unit 110, the prediction data generation unit 130, the display control unit 150 included in the surgery support apparatus 10 are included in the central processing device.

Hereinafter, the surgical navigation system 100 of the present embodiment will be described with reference to FIG. 2. The surgical navigation system 100 of the present embodiment includes the surgery support apparatus 10, the display (display apparatus) 20 that displays position information, etc. provided from the surgery support apparatus 10, a medical image database 50 communicably connected to the surgery support apparatus 10 via a network 40, and the position measuring apparatus 30 that measures the position of the surgical tool, etc.

The surgery support apparatus 10 includes the central processing device 11, a main memory 12, a storage device 13, a display memory 14, a controller 15, and a network adapter 16. These components included in the surgery support apparatus 10 are connected to each other via a system bus 17. In addition, a keyboard 19 is connected to the system bus 17, and a mouse 18 is connected to the controller 15. The mouse 18 and the keyboard 19 function as an input apparatus for receiving input of a processing condition for a medical image. Note that the mouse 18 may correspond to another pointing device such as a trackpad or a trackball, and the display 20 may have a touch panel function, thereby replacing the functions of the mouse 18 and the keyboard 19.

Figure 3:
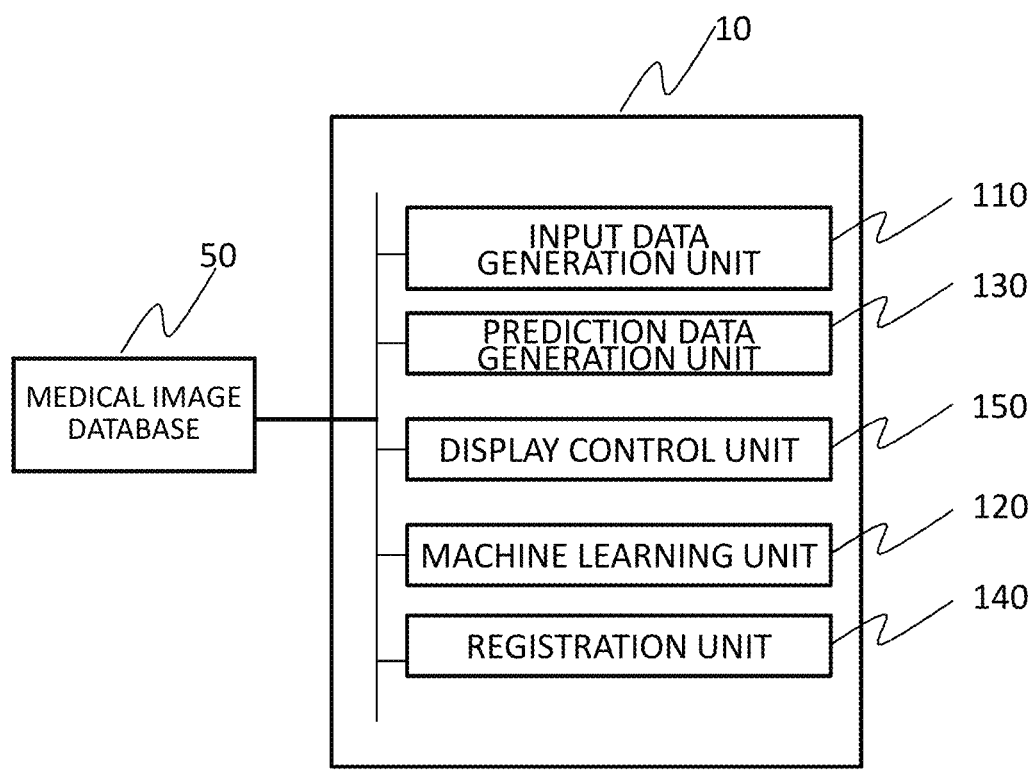
FIG. 3 is a block diagram of a configuration of a central processing device of the surgery support apparatus according to the first embodiment.

The central processing device 11 controls the entire surgery support apparatus 10 and performs predetermined arithmetic processing on a medical image or position information measured by the position measuring apparatus 30 according to a processing condition input via the mouse 18 or the keyboard 19. For this reason, the central processing device 11 implements functions of the input data generation unit 110, the prediction data generation unit 130, the display control unit 150, etc. In addition to these functions, as illustrated in FIG. 3, the central processing device 11 may include a registration unit 140, etc. for aligning a position in real space coordinates measured by the position measuring apparatus with a position in image coordinates, and a machine learning unit 120 in the case of creating a learned AI algorithm.

The input data generation unit 110 generates input data indicating information related to an object including a shape of the object before the intervention based on the processing condition input by the input apparatus such as the mouse 18 and the medical image read from the medical image database 50. The input data is information necessary to generate prediction data that predicts the shape of the object after the intervention, and corresponds to the input data used to create the learned AI algorithm. Specifically, as the input data, a two-dimensional (2D) or 3D medical image read from the medical image database 50, a segmentation image obtained by extracting a feature region of the object from the medical image by image processing, a feature point extracted by image processing, etc. are generated. When the object is a brain, a skull, brain parenchyma, a brain tumor, etc. are considered as feature regions, and these feature regions may be extracted using a known segmentation method and used as a segmentation image. Further, any point included in a contour of such a feature region can be set as a feature point.

The prediction data generation unit 130 generates prediction data predicting an intervention site from data before an intervention based on the input data generated by the input data generation unit 110 using an artificial intelligence algorithm stored in the storage device 13. Details of the artificial intelligence algorithm and generation of the prediction data will be described later.

The main memory 12 stores a program executed by the central processing device 11 and the progress of arithmetic processing.

The storage device 13 stores an artificial intelligence algorithm learning a rule for finding an appropriate intervention site from data before the intervention by analyzing data before the intervention and the intervention site for the object. The storage device 13 further stores a program executed by the central processing device 11 and data necessary for executing the program. Furthermore, the storage device 13 stores a medical image (image data) read from the medical image database 50 and related medical information related to the medical image. The related medical information may include surgery-related information related to the object or the target organ, such as a tumor site, a tumor region, or histopathological diagnosis, and information related to a factor considered to influence the intervention site in addition to a diagnosis name, age, gender, and a body position at the time of medical image capturing. As the storage device 13, for example, it is possible to apply a device that can exchange data with a portable recording medium such as a CD/DVD such as a hard disk, a USB memory, or an SD card.

The display memory 14 temporarily stores display data for causing the display apparatus 20 to display an image, etc.

The controller 15 detects a state of the mouse 18, acquires a position of a mouse pointer on the display 20, and outputs the acquired position information, etc. to the central processing device 11. The network adapter 16 connects the surgery support apparatus 10 to the network 40 including a local area network (LAN), a telephone line, or the Internet.

The display 20 displays the medical image on which the position information generated by the surgery support apparatus 10 is superimposed, thereby providing the surgeon with the medical image and the position information of the surgical tool, etc.

The medical image database 50 stores a medical image such as a tomographic image of the patient and related medical information related to the medical image. As the medical image stored in the medical image database 50, for example, an image captured by a medical image capturing apparatus such as an MRI apparatus, a CT apparatus, an ultrasonic imaging apparatus, a scintillation camera apparatus, a PET apparatus, or a SPECT apparatus is preferably used. Image data such as a segmentation image created by an imaging apparatus or an image processing apparatus other than the surgery support apparatus 10 may be stored together with the original image data.

The medical image database 50 is connected to the network adapter 16 via the network 40 so that signals can be transmitted and received. Here, "so that signals can be transmitted and received" refers to a state in which signals can be transmitted and received to each other or from one side to the other, regardless of whether connection is electrically or optically wired or wireless.

Figure 4:
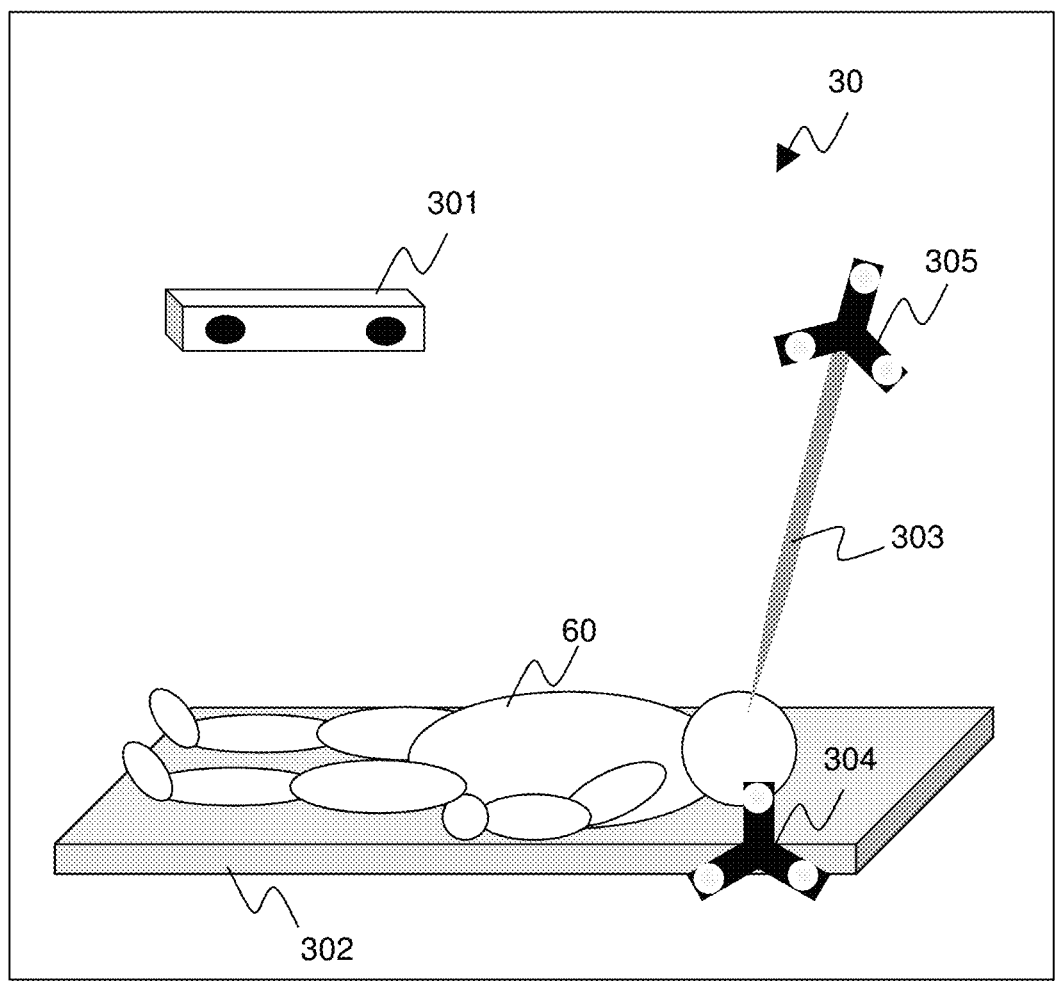
FIG. 4 is an explanatory diagram illustrating a schematic configuration of a position measuring apparatus in the surgical navigation system of FIG. 2.

The position measuring apparatus 30 measures a 3D position of a surgical tool, etc. in a subject after the intervention of surgery, etc. For example, as illustrated in FIG. 4, the position measuring apparatus 30 includes one or a plurality of infrared cameras 301 fixed in the operating room. Meanwhile, markers 304 and 305 that emit light detectable by the infrared camera 301 from a plurality of locations are provided near the subject (patient) 60 on a bed 302 and in a surgical tool 303, and position information indicating a position of the surgical tool 303, etc. in the patient 60 is acquired by measuring light from the markers 304 and 305 using the infrared camera 301. The position measuring apparatus 30 outputs the acquired position information to the central processing device 11 via the system bus 117 in the surgery support apparatus 10.

Next, generation of the AI algorithm stored in the storage device 13 will be described.

As described above, the AI algorithm stored in the storage device 13 is an AI algorithm learning a rule for finding an appropriate intervention site from data before the intervention, and is generated using the surgery support apparatus 10 or another computer.

Hereinafter, a generation procedure will be described using a case where an AI algorithm learning a rule for finding an appropriate craniotomy site (intervention position) from data before craniotomy in craniotomy is generated in the surgery support apparatus 10 as an example. In this case, as illustrated in FIG. 3, the central processing device 11 of the surgery support apparatus 10 includes a machine learning unit 120 in addition to the input data generation unit 110 and prediction data generation unit 130 described above. In addition, it is presumed that the medical image database 50 stores medical images before and after the intervention, that is, before and after craniotomy together with the related medical information thereof.

Figure 5:
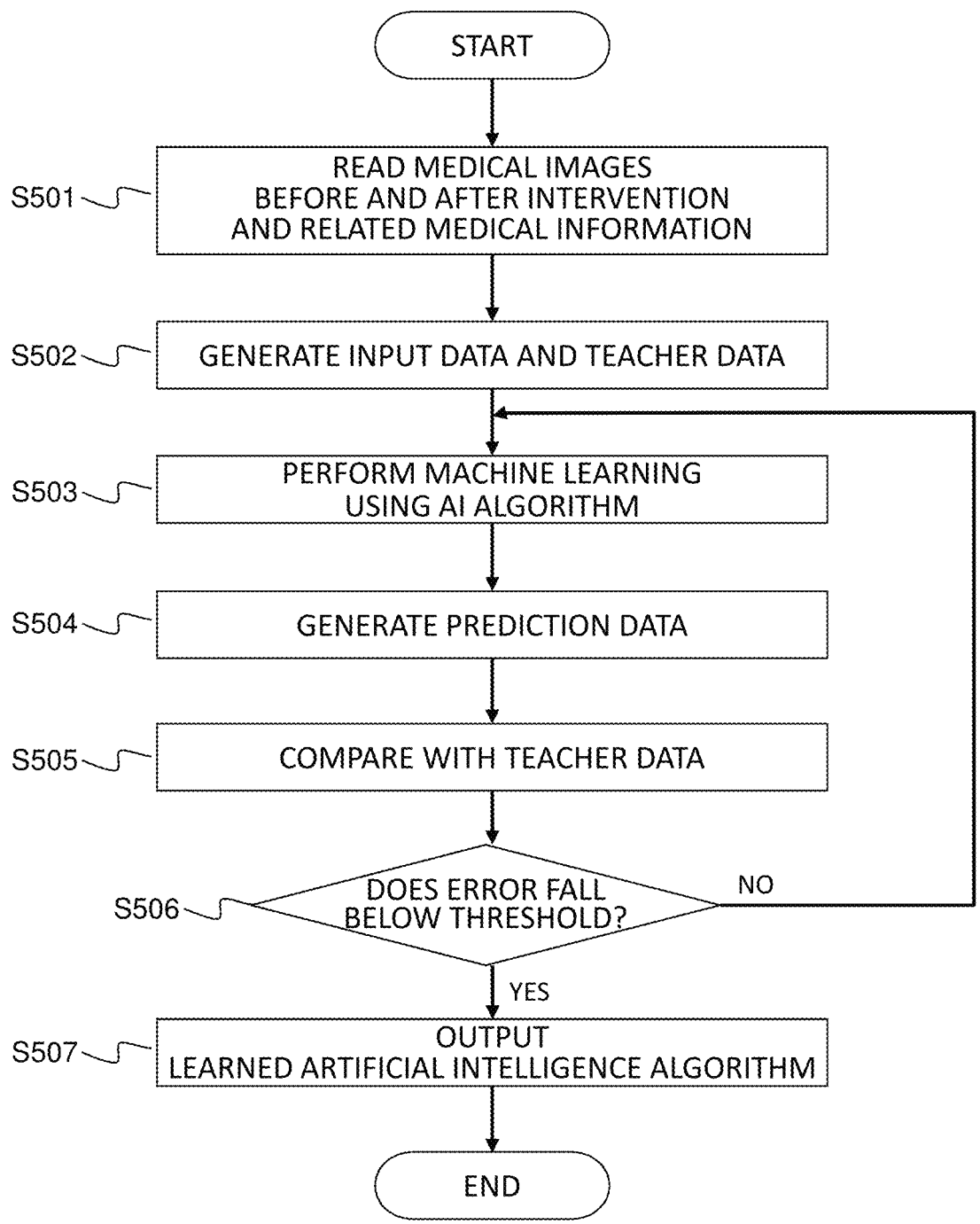
FIG. 5 is a flowchart describing a process of generating an artificial intelligence algorithm applied to the surgery support apparatus of the first embodiment.

Referring to generation of the AI algorithm, as illustrated in FIG. 5, first, in step S501, the central processing device 11 (input data generation unit 110) reads medical images before and after the intervention, that is, before and after craniotomy and related medical information related to the medical images from the medical image database 50.

Subsequently, in step S502, the input data generation unit 110 generates input data and teacher data to be input to the artificial intelligence algorithm and learned based on the medical images and the related medical information read in step S501.

As the input data, as described above, in addition to the medical images, a segmentation image obtained by extracting a feature region from a medical image or a feature point can be used as the input data. Here, it is presumed that the brain parenchyma, skull, and tumor are segmented from the MRI image of the brain. Segmentation is a technology for extracting a desired organ or site from a medical image and generating an image of only the organ or only the site. It is possible to use a known method such as Snakes, a level set method, or a method based on deep learning. Further, an image of only the tumor region may be extracted, and a binary image representing the presence or absence of a tumor may be used. As the MRI image of the brain, for example, it is possible to use a T1 image (or T1 weighted image) and a T2 image (or T2 weighted image) of the MRI of the brain parenchyma before surgery. These images are images depicting the brain parenchyma and tumor with different contrasts, and can be accurately segmented. In addition, it is possible to use a fluid-attenuated inversion recovery (FRAIR) image, etc. having excellent ability to visualize lesions.

A plurality of images may be used as the input data. In this case, the images are aligned so as not to be shifted from each other. Specifically, alignment is performed by applying a transformation matrix (here, limited to translation and rotation) to one image so as to maximize similarity between two images. As the similarity, it is possible to use zero mean normalized cross-correlation (ZNCC), sum of squared differences (SSD), sum of absolute differences (SAD), normalized cross-correlation (NCC), and mutual information.

The teacher data is data indicating intervention position information. Specifically, it is possible to select a segmentation image of a craniotomy region (a portion of a skull to be resected), a feature amount such as a center of gravity or a radius of the craniotomy region, etc. In the present embodiment, an image of a craniotomy region is extracted from a 3D binary image of a skull obtained from a medical image such as an MRI image using, for example, a region expanding method, and the binarized image is used as teacher data. Alternatively, the extracted craniotomy region may be approximated by a simple figure, and a feature amount representing the figure may be used as teacher data. For example, in the case of approximating by a circle, the center of gravity and the radius may be used as teacher data. The input data and the teacher data are aligned so that there is no shift. Further, the craniotomy region may correspond to a region obtained by dividing the brain into relatively large regions (frontal lobe, temporal lobe, etc.).

Figure 6:
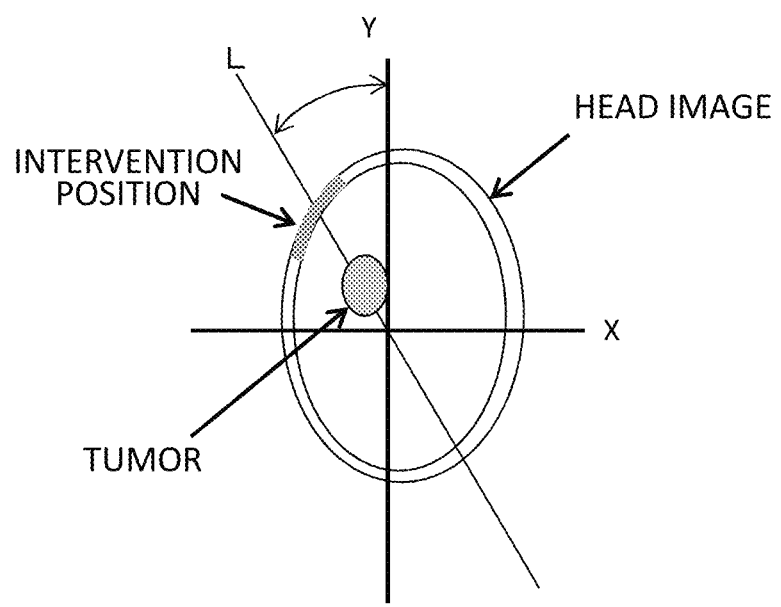
FIG. 6 is an explanatory diagram illustrating a relationship between an intervention position and a posture.

The teacher data may include a posture (head position) of a head of the patient in addition to the data indicating the craniotomy region. In particular, in brain surgery involving incision of the skull, it is important to set the craniotomy position to an upper part in a vertical direction so that a cerebrospinal fluid, etc. in the skull do not spill outside, and it is necessary to set a posture of the head so that the craniotomy position is in the upper part. As the data related to the posture of the head used as the teacher data, for example, as illustrated in FIG. 6, it is possible to use an inclination from a coordinate axis (for example, Y-axis) represented by the Euler angle based on coordinates of the head image corresponding to the input data. Alternatively, an image obtained by rotating the head image such that a line L connecting the target site of the surgery and a center of the craniotomy region coincides with the coordinate axis (vertical axis) of the reference coordinates may be used as the teacher data.

When the input data generation unit 110 completes generation of the input data and the teacher data insteps S501 and S502 described above, the machine learning unit 120 starts a machine learning process of steps S503 to S505 using the artificial intelligence algorithm before learning. That is, the input data is substituted into the artificial intelligence algorithm before learning in step S503, prediction data is acquired in step S504, and the obtained prediction data is compared with the teacher data in step S505. Then, a result of comparison is fed back to the artificial intelligence algorithm and corrected, that is, by repeating processing of step S503 to step S505, the artificial intelligence algorithm is optimized so that an error between the prediction data and the teacher data is minimized.

Figure 7:
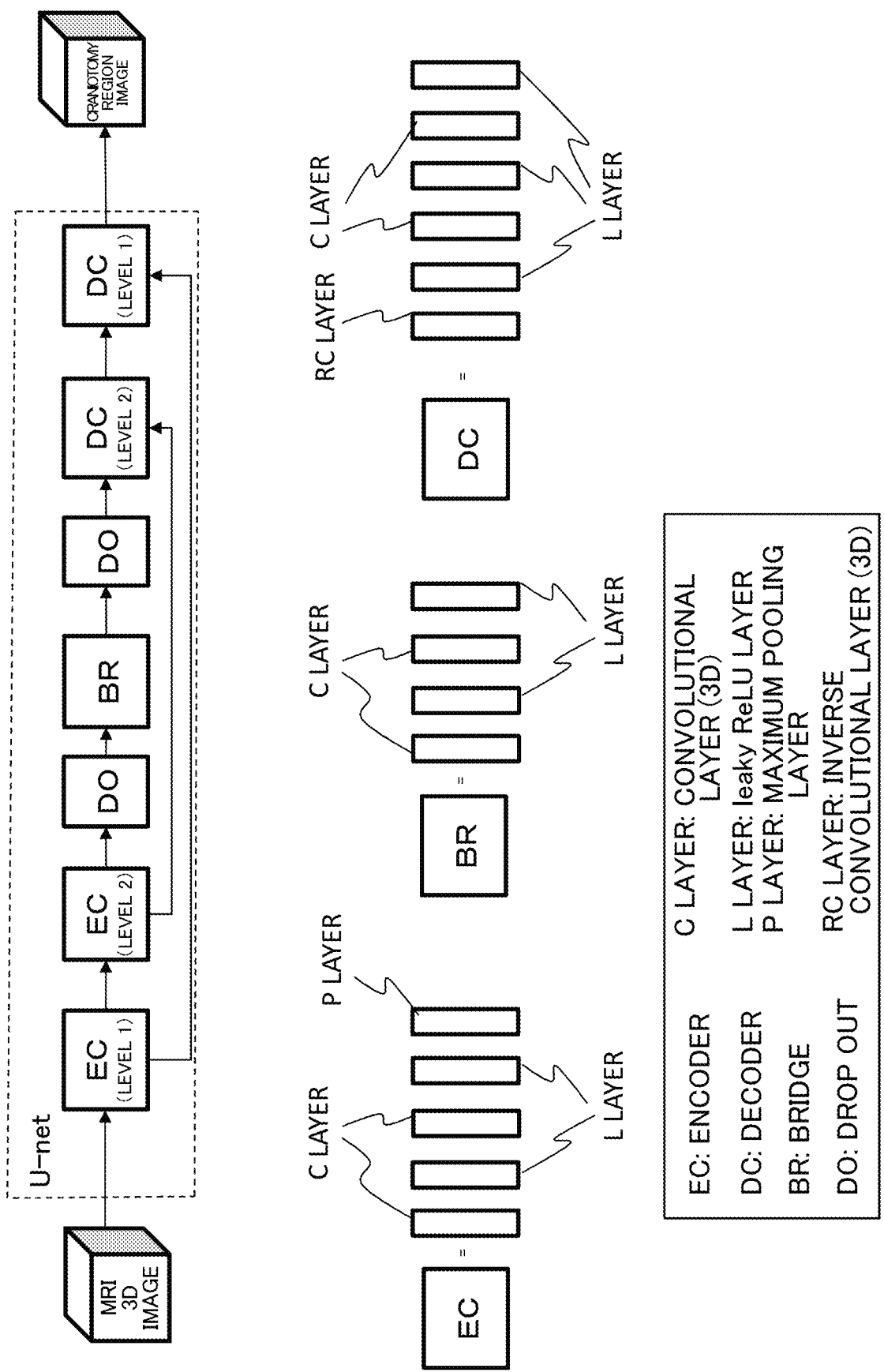
FIG. 7 is a diagram illustrating an example of an artificial intelligence algorithm applied to the surgery support apparatus.

As the artificial intelligence algorithm, for example, it is preferable to use an AI algorithm of deep learning (deep learning) such as a convolutional neural network. Specifically, a known AI algorithm such as U-net, Seg-net, or DenseNet can be used as the AI algorithm. As an example, a structure of U-net is illustrated in FIG. 7. As illustrated in the figure, U-net is a network having a structure in which a plurality of encoders EC and the same number of decoders DC are connected via a bridge BR, and an encoder EC and a decoder DC having the same level are connected to each other. As illustrated in a lower part of the same figure, each of the encoders, the decoders, and the bridge has a structure in which a convolutional layer (C layer), a ReLU (ramp function) layer, a leaky ReLU layer (L layer), etc. are stacked. U-net can compensate for the detail of pixels that disappears during a feature propagation process by directly connecting the encoder and decoder of each layer, and has a feature in which a result is obtained with a relatively small amount of calculation and a short calculation time. In the illustrated example, the input data is an MRI image (for example, a segment image), and the output prediction data is a craniotomy region image (for example, a binarized image), which is learned using, for example, hundreds of pieces or more of brain tumor data.

In step S505, as an evaluation function for evaluating the error between the prediction data and the teacher data, it is possible to use an index such as a mean absolute error or a root mean squared error. In the present embodiment, for example, the AI algorithm (U-net) is learned so as to minimize the average absolute error, and when the average absolute error falls below a predetermined value (S506), U-net is considered to be optimized and output as the learned AI algorithm in step S507.

The AI algorithm (learned AI algorithm) optimized in this way has the same function as that of a function of outputting specific data with respect to input data, and is an AI algorithm for surgery support that outputs prediction data of an intervention site with respect to input data before the intervention in the present embodiment. The prediction data of the intervention site is determined by the teacher data used for learning, and corresponds to a binary image (craniotomy region image) in which only the craniotomy region is extracted, a binary image representing a boundary of the craniotomy region, a feature amount representing a simple figure when the craniotomy region is approximated by the figure, etc. in the present embodiment. In addition, when the teacher data includes a body position (head posture), the recommended body position is output as prediction data. The learned AI algorithm output by the machine learning unit 120 is stored in the storage device 13.

Next, a description will be given of a specific example of the surgical navigation using the learned AI algorithm. The surgical navigation system 100 of the present embodiment can execute two functions of presenting information related to the intervention position and presenting position information of the surgical tool.

Figure 8:
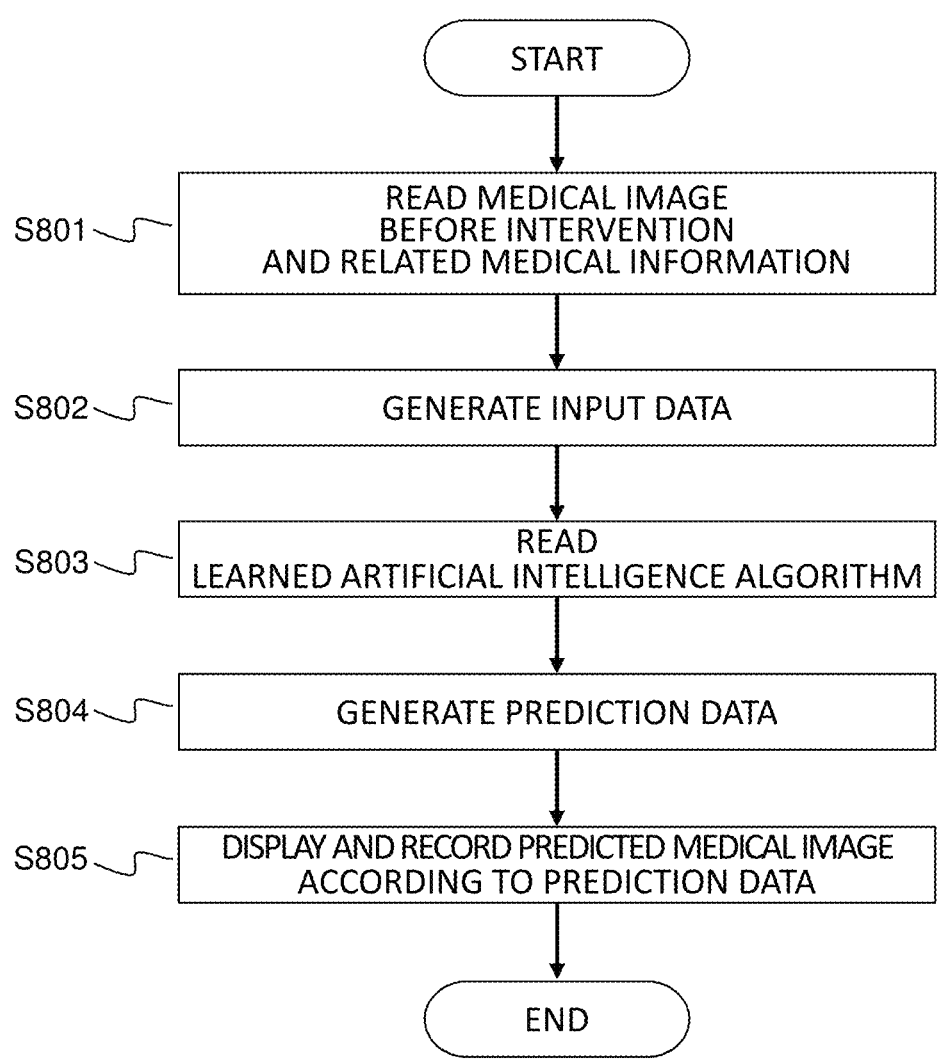
FIG. 8 is a flowchart describing a process of generating prediction data in the surgery support apparatus of the first embodiment.

First, generation of prediction data and presentation of an intervention position using the learned AI algorithm will be described with reference to a flowchart of FIG. 8. Here, a case where a craniotomy region image is output as prediction data will be described as an example.

First, in step S801, the input data generation unit 110 reads, from the medical image database 50, a medical image captured before the intervention, that is, before craniotomy, and related medical information for a patient corresponding to a surgery target. Subsequently, in step S802, input data to be input to the learned AI algorithm is generated based on the data read in step S801. A procedure for generating the input data is the same as the procedure for generating the input data in step S502 of FIG. 5, and generates the same type of data as the input data used for learning the AI algorithm. The input data corresponds to, for example, a T1 image, a T2 image, and a tumor image of the brain parenchyma of the patient. All of these images may be used, or the images may be used in combination.

In step S803, the prediction data generation unit 130 reads the learned AI algorithm stored in the storage device 13, substitutes the input data created in step S802 into the learned AI algorithm, performs an operation, and outputs prediction data (S804). In the present embodiment, the operation is performed in accordance with U-net of FIG. 7, and image data of the craniotomy region is obtained as prediction data. In step S805, the display control unit 150 receives the image data of the craniotomy region generated by the prediction data generation unit 130, and causes the display 20 to display the image data via the display memory 14.

Figure 9:
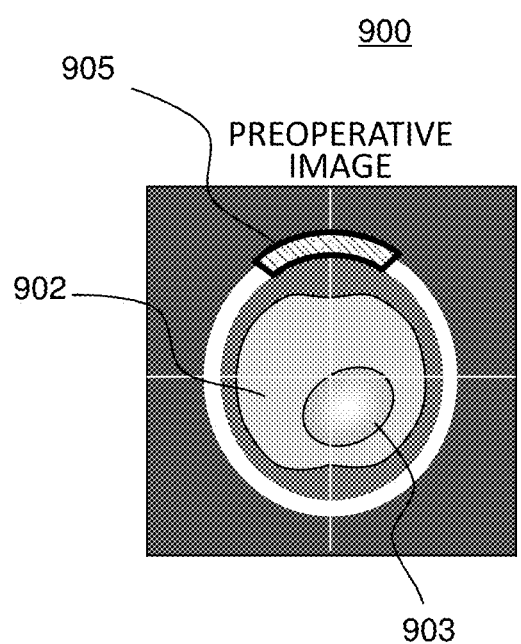
FIG. 9 is a diagram illustrating an example of a display screen displayed on a display apparatus in the surgery support apparatus of the first embodiment.

Examples of a display screen 900 of a medical image before the intervention, that is, a preoperative image displayed on the display 20 are illustrated in FIG. 9 and FIGS. 10A and 10B. In the example illustrated in FIG. 9, an image (binary image) 905 indicating a craniotomy region image is displayed superimposed on an MRI image of the brain before the intervention including brain parenchyma 902 and a brain tumor 903. From such a display, the surgeon can detect a position and a size of the craniotomy area, and can use this display as support information to proceed with preparation for craniotomy.

Note that even though FIG. 9 displays only an image of an axial plane, it is possible to simultaneously display an image of another plane such as a sagittal plane or a coronal plane, or a rendering image, and it is possible to superimpose and display a craniotomy region image of the sagittal plane or the coronal plane, or a rendering image of the craniotomy region on the images.

FIGS. 10A and 10B illustrate display examples of a case where data related to the posture of the head is output in addition to the image data of the craniotomy region as the prediction data. In the example illustrated in FIG. 10A, upon receiving the Euler angle of the posture of the head (posture recommended as the posture during surgery: recommended posture) as the prediction data from the prediction data generation unit 130, the display control unit 150 superimposes a line segment 910 having an inclination with respect to image coordinates by an angle of the prediction data on the preoperative image and transfers the line segment 910 to the display memory 14. In this way, as illustrated in the figure, the line segment 910 connecting a center of the craniotomy region and the center of gravity of the tumor is displayed on the preoperative image. FIG. 10B illustrates an image in which the craniotomy region is superimposed on the preoperative image by rotating the image so that the line connecting the center of the craniotomy region and the center of gravity of the tumor coincides with the coordinate axis (Y-axis: vertical direction) of the image. By these displays, the surgeon can visually detect a degree of tilting the head at which craniotomy may be performed.

Note that the prediction data generated by the prediction data generation unit 130 is stored in the storage device 13 or the medical image database 50 as necessary. In this way, the prediction data can be used for ex-post confirmation/verification, AI algorithm learning, etc.

Next, a description will be given of a surgical navigation process including presentation of the intervention position and presentation of the surgical tool position described above with reference to a flowchart of FIG. 11.

First, in step S811, the central processing device 11 acquires, from the medical image database 50, a medical image captured before surgery for the patient corresponding to a surgery target and a prediction medical image indicating a shape of the object after the intervention as prediction data generated by the prediction data generation unit 130. In step S812, a medical image used for navigation and a position and a direction (position in image space coordinates) of the subject in a predicted medical image are acquired from digital imaging and communication in medicine (DICOM) information of the acquired medical image, the related medical information, and information related to the predicted medical image.

In step S813, as illustrated in FIG. 4, using the position measuring apparatus 30, the central processing device 11 measures the position information of the marker 304 placed near the subject 60 and detects a position (position in real space coordinates) of the subject 60. As the position of the marker 304, it is possible to detect a position in 3D real space by detecting three or more optically or magnetically detectable spherical markers fixed to the marker 304 using the position measuring apparatus 30. In addition, for example, a position of the subject 60 can be detected by measuring a position when the marker 304 is temporarily placed on a predetermined site (for example, the head) of the subject 60 and a position to be fixed when surgery is conducted in advance, and comprehending a relationship between these two positions.

In step S814, the registration unit 140 of the central processing device 11 calculates a position on the medical image corresponding to a subject position from the position information (position in the image space coordinates) of the subject in the medical image obtained in step S812 and the position information (position in the real space coordinates) of the subject obtained in step S813, thereby performing alignment (registration) of the position of the subject and the position on the medical image.

Meanwhile, in step S815, the input data generation unit 110 and the prediction data generation unit 130 calculate an intervention site and a recommended posture on the image. This step is the same as the processing described in the flow of FIG. 8 (steps S802 to S804), in which the input data generation unit 110 generates input data from the preoperative image of the subject acquired in step S812, and the prediction data generation unit 130 generates, for example, a craniotomy region and a recommended posture as the prediction data using the learned AI algorithm.

In step S816, the position information of the surgical tool is measured to guide the operation of the surgical tool, etc. That is, the central processing device 11 measures the position (position in the real space coordinates) of the marker 305 provided on the surgical tool 303 using the position measuring apparatus 30, and performs coordinate transformation thereon to calculate coordinates of the marker 305 in a medical image coordinate system. Note that it is presumed that the position information of the marker 305 includes an offset to a distal end of the surgical tool 303.

In step S817, the display control unit 150 generates a navigation image in which the intervention site (the craniotomy region) obtained in step S815 and the position information of the surgical tool, etc. obtained in step S816 are superimposed on the medical image, and causes the display 20 to display the generated navigation image via the display memory 14. In this instance, the medical image before the intervention acquired before surgery is used as the medical image on which the position information of the surgical tool, etc. is superimposed and displayed. At this time, as necessary, a desired image processing condition (parameter, etc.) may be input via the input apparatus such as the mouse 18 or the keyboard 19, and the central processing device 11 (display control unit 150) generates a navigation image subjected to processing according to the input image processing condition.

Each of the above-described steps may be performed at a timing desired by a user, or any one of the steps may be continuously performed during surgery. FIG. 11 illustrates a case where measurement of the surgical tool (S816) is continuously performed. In this case, each time the position of the surgical tool 303 changes, calculation of the coordinates of the marker 305 in a medical image coordinate system (S816) and display of the surgical tool position (S817) are updated and performed. These steps are continued until the surgery is completed (S818) or until a termination instruction is given via the input apparatus.

FIG. 12 illustrates a display example of a navigation image in which both the intervention site and the surgical tool position are displayed by the surgical navigation system according to the present embodiment.

A display screen 900 illustrated in FIG. 12 displays, as a navigation image, a virtual surgical tool (surgical tool icon) 904 formed according to alignment information superimposed on an axial cross section 911, a sagittal cross section 912, and a coronal cross section 913, which are three orthogonal cross-sectional images of the surgical site of the subject 60, and a 3D rendering image 914. In addition, the predicted intervention site 905 is displayed in an overlapping manner.

In the illustrated example, the right side of the screen 900 displaying an image corresponds to an interface display screen for receiving an instruction or designation from the user. At a top, a position acquisition icon 921 for commanding position measurement of the subject, a registration icon 922 for executing alignment between a real space position and an image space position, and an intervention site prediction icon 923 that displays a medical image on which the predicted intervention site 915 is superimposed and displayed are displayed.

When the instruction or designation from the user is received via such an interface, steps S813 to S815 illustrated in FIG. 11 are activated by the instruction from the user. For example, the user presses the position acquisition icon 921 to receive a measurement instruction of the subject position by the position measuring apparatus 30 (S813), presses the registration icon 922 to calculate a position of the subject on the medical image according to the position information of the subject measured by the position measuring apparatus 30 (S814), and aligns the position of the subject with the position on the medical image. In addition, the intervention site prediction icon 923 is pressed to cause the display 20 to display the medical image on which the predicted intervention site is superimposed (S815).

In addition, in a lower right part of the image display screen 900, icons of an image threshold interface 931 for inputting an image processing command, a viewpoint position translation interface 932, a viewpoint position rotation interface 933, and an image enlargement interface 934 are displayed. By operating the image threshold interface 931, a display region of the medical image can be adjusted. In addition, the viewpoint position translation interface 932 can translate the viewpoint position with respect to the medical image in parallel, and the viewpoint position rotation interface 933 can rotationally moved the viewpoint position. Further, the selected region can be enlarged by the image enlargement interface 934.

Note that FIG. 12 illustrates a case where three orthogonal cross-sectional images of the surgical site are used as the navigation image. However, the invention is not limited thereto. For example, an icon indicating the surgical tool may be superimposed and displayed on the preoperative image on the display screen 900 illustrated in FIG. 9.

In any case, by displaying the surgical tool icon 904 in real time, the surgeon can understand a predicted positional relationship with the intervention site 905, and can appropriately intervene in the subject 60.

As described above, according to the present embodiment, alignment information necessary for alignment between the subject position and the image position is generated from position information of the subject 60, the bed whose relative positional relationship with the subject 60 does not change, or the marker 304 fixed to a rigid body such as a fixture measured by the position measuring apparatus 30, and DICOM information corresponding to image position information attached to the medical image. Further, a navigation image in which position information of the surgical tool 303 acquired from the marker 305 provided on the surgical tool 303 is virtually superimposed on the medical image can be generated and displayed on the display 20. In this instance, by superimposing the image of the predicted intervention site, the surgeon can perform an appropriate intervention, and thus the accuracy of the intervention can be improved.

Note that when a predicted result for 65 cases was compared with an actual result using the AI algorithm used in the present embodiment and evaluated, an overlapping degree between the craniotomy region obtained as the prediction data and the actual craniotomy region (Dice coefficient) showed a value of 0.6 or more (overlapping degree of 60% or more), and an excellent result was obtained. In particular, 100% coincidence was obtained for coincidence with a region of the brain.

Note that even though the present embodiment describes the craniotomy of the brain surgery, the invention is applicable to surgery on other body sites. For example, the invention can be applied to a laparotomy position in laparotomy for a digestive organ such as a liver or an open chest operation for a heart.

Second Embodiment

The present embodiment has a feature in that a function of predicting movement or deformation of an organ after an intervention is further added using information of a predicted intervention site.

In some cases, an organ such as the brain may move or deform by the intervention (for example, craniotomy). For example, as illustrated in FIG. 13A, in a tomographic image of the brain before craniotomy, a brain parenchyma 902 and a brain tumor 903 are present in a region surrounded by a skull 901. Here, in the case of performing surgery to remove the brain tumor 903, when the skull 901 and a part of the dura are cut off and a craniotomy range 906 is formed, as illustrated in FIG. 13B, the brain parenchyma 902 and the brain tumor 903 floating in cerebrospinal fluid are moved and deformed from a position before craniotomy due to an influence of gravity, etc. Such a phenomenon is referred to as a brain shift. The brain shift involves movement or deformation of the brain from a few mm to a few cm. For this reason, in the surgical navigation using the image before the intervention, even when the surgical tool position is displayed on the image, reliability of the position information is impaired. In addition, the brain shift is greatly affected by the intervention position. The present embodiment improves the accuracy of surgical navigation by adding information about the intervention position to predict deformation, etc. after the intervention (brain shift).

Figure 2:
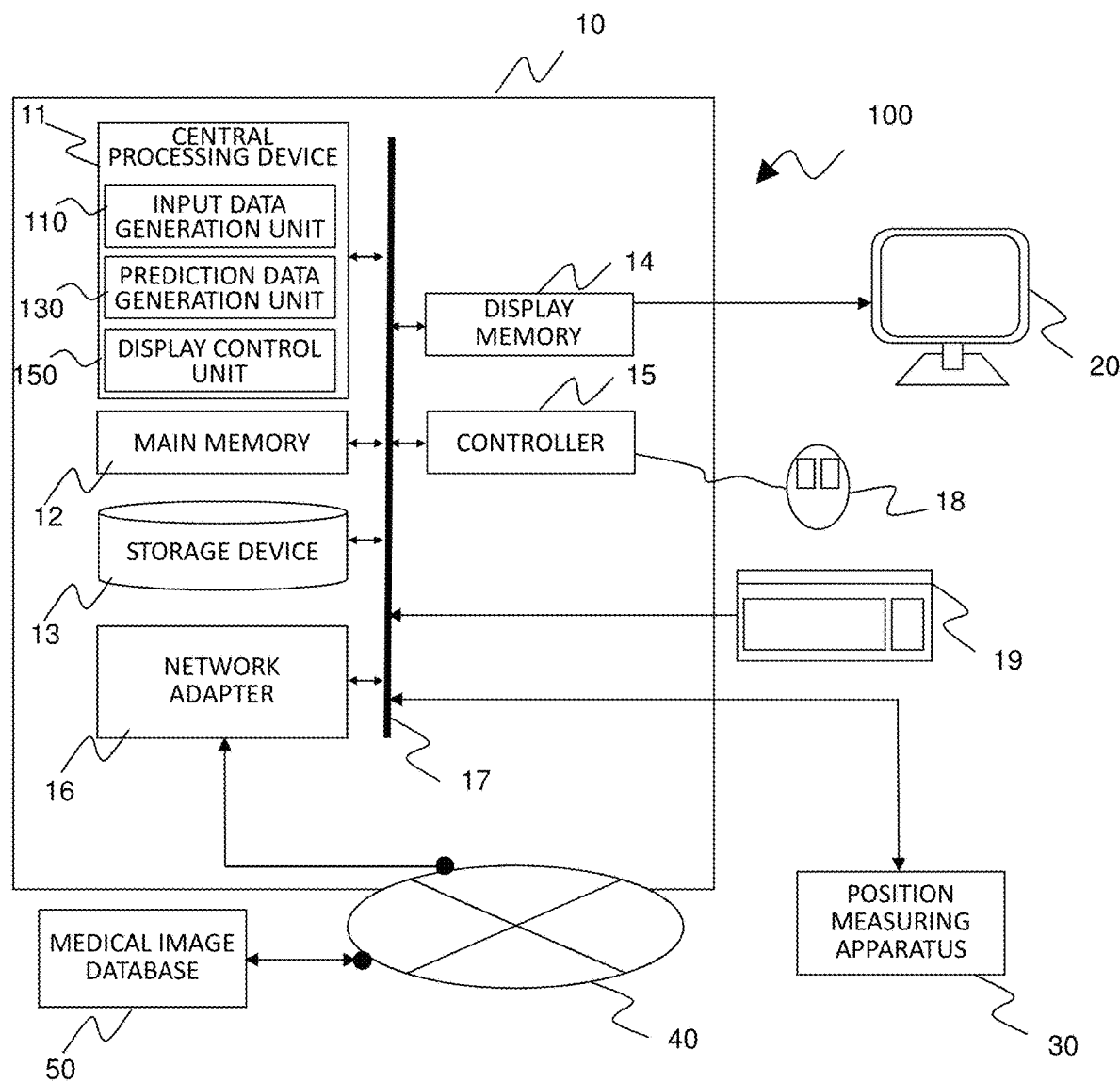
FIG. 2 is a block diagram illustrating a configuration of a surgery support apparatus of a first embodiment and a surgical navigation system including the same.

In the present embodiment, prediction of the intervention site is similar to that in the first embodiment, and a main configuration for implementing the present embodiment is similar to that illustrated in FIG. 2. Hereinafter, the present embodiment will be described focusing on a difference from the first embodiment.

A configuration of a central processing device 11 of the present embodiment is illustrated in FIG. 14. As illustrated in the figure, the central processing device 11 of the present embodiment includes an input data generation unit 110, a first prediction data generation unit 131, and a second prediction data generation unit 132. In addition, a storage device 13 stores a first learned AI algorithm learned to predict an intervention position and a second learned AI algorithm for predicting movement/deformation of an organ, etc. after the intervention. When the second learned AI algorithm is created in the central processing device 11, the central processing device 11 includes a machine learning unit 120 as in the central processing device of FIG. 3.

The first learned AI algorithm is similar to the learned AI algorithm of the first embodiment, and outputs prediction data of an intervention position using an image before the intervention, etc. as input data.

The second learned AI algorithm is obtained by learning a deformation rule of an object such as an organ deformed due to the intervention. For example, an image including an organ moved/deformed after the intervention is output using an image including an organ before the intervention and prediction data (intervention position information) of the first learned AI algorithm illustrated in FIGS. 13A and 13B as input data. However, the input data is not limited to the medical image, and may correspond to a segmentation image or a feature point obtained by extracting a feature region from the medical image. The teacher data (output data) may correspond to, for example, a displacement field matrix that associates movement and deformation of the object before and after the intervention. The displacement field matrix is, for example, a map that defines values (Δx, Δy) to be added to pixel values (x, y) for each pixel of an image as illustrated in FIG. 15. When the output data corresponds to the displacement field matrix, the deformation rule itself is directly learned, and an improvement inaccuracy can be expected. However, the output data is not limited thereto, and may correspond to a medical image, a segmentation image, a feature point, etc. after the intervention.

In addition, as the AI algorithm used for learning, it is preferable to use an AI algorithm for deep learning such as a convolutional neural network similarly to the first learned AI algorithm. An example of U-net used for the second AI algorithm is illustrated in FIG. 16. A structure of U-net is similar to that illustrated in FIG. 7. In this example, the input data is a 3D MRI image (T1 image and T2 image) of the brain parenchyma before the intervention and a 3D image (intervention site image) representing the intervention site, and the teacher data is a displacement field matrix (displacement field map) illustrated in FIG. 15 indicating a position in the MRI image during surgery to which each point of the MRI image before surgery moves. In addition, as the intervention site image of the input data, it is possible to use an intervention image corresponding to an output (prediction data) of the first learned AI algorithm, for example, a binary image in which an intervention site is set to 1 and others are set to 0. However, the image representing the intervention site may not correspond to a binary image. For example, it is possible to adopt an image in which a portion at which a probability of the intervention site is the highest is set to 1, a portion at which the probability is the lowest is set to 0, and a probability therebetween has a value between 0 and 1.

Note that the artificial intelligence algorithm may not correspond to U-net, and may correspond to another algorithm such as Seg-net or DenseNet.

Next, surgical navigation processing (mainly processing of the central processing device) according to the present embodiment will be described with reference to a flowchart of FIG. 17. Note that in FIG. 17, steps having the same contents as those of FIG. 11 are denoted by the same reference numerals, and redundant description will be omitted.

First, a medical image is read, each of position information and subject position information thereof is calculated, and registration information is calculated (S820 (S811 to S814)). Subsequently, input data is generated from the read medical image, and the first prediction data generation unit 131 calculates an intervention site and a posture on the image using the first learned AI algorithm (S815). Subsequently, in step S821, the second prediction data generation unit 132 inputs the information of the intervention site predicted in step S815 and the input data generated in step S815 to the second learned AI algorithm, and acquires the displacement field matrix (FIG. 15) representing movement/ deformation of the brain parenchyma after the intervention as prediction data. Furthermore, by applying this displacement field matrix to the image before the intervention, an image after the intervention can be obtained as illustrated in FIG. 13B.

As a method of applying the displacement field matrix, an X'-coordinate and a Y'-coordinate of a destination are obtained by adding ΔX and ΔY (X value and Y value of a point corresponding to the same pixel in the displacement field matrix) to X-coordinate and Y-coordinate of each pixel of the MRI image, respectively. An image in which a pixel value of a pixel at the X'-coordinate and the Y'-coordinate is set to a pixel value of a pixel before movement corresponds to a predicted image after the brain shift. Generation of the image after the intervention using such a displacement field matrix may be performed by the second prediction data generation unit 132, or a separate operation unit (not illustrated) may be provided in the central processing device 11 to perform the generation using the operation unit.

Meanwhile, in step S816, the registration unit 140 calculates the position of the subject on the medical image according to the position information of the subject measured by the position measuring apparatus 30 (S816), aligns the position of the subject with the position on the medical image, measures the position of the surgical tool (marker) measured by the position measuring apparatus 30, and performs coordinate transformation thereon to calculate coordinates of the marker in the medical image coordinate system.

Thereafter, the display control unit 150 causes the display 20 to display an image in which a virtual surgical tool is superimposed on the medical image. Here, before the intervention, the image before the intervention is used as the medical image, and the intervention site image and the surgical tool icon are displayed so as to be superimposed on the image before the intervention (S822 and S823). After the intervention, the image after the intervention predicted in step S821 is displayed as the medical image, and the surgical tool position is displayed so as to be superimposed on the image (S822 and S824).

As described above, according to the present embodiment, since the brain shift (image after the intervention) is predicted by adding the information of the intervention position, and the position information of the surgical tool, etc. is presented for the image after the brain shift, accuracy of the surgical navigation can be greatly improved.

What is claimed is:

1. A surgery support apparatus for supporting an intervention and treatment in an object in a living body by displaying an image, the surgery support apparatus comprising a prediction data generation unit that uses a first learned artificial intelligence algorithm learned using image data including the object before the intervention or data obtained by processing the image data and information related to an intervention position on a surface of the living body to predict an intervention position in the living body to be treated, and outputs prediction data; and a second prediction data generation unit that uses a second learned artificial intelligence algorithm learned using an image and an intervention position before the intervention and an image after the intervention to predict an image after the intervention for the living body to be treated, wherein the second prediction data generation unit inputs a first advance image acquired in advance for the living body to the treated and prediction data generated by the prediction data generation unit to the second learned artificial intelligence algorithm, and predicts a position change of the object after the intervention.

2. The surgery support apparatus according to claim 1, wherein the information related to the intervention position includes any one of coordinates of one point of the intervention position in an image space, a predetermined region including the coordinates of the one point, and a predetermined shape specified by the coordinates of the one point.

3. The surgery support apparatus according to claim 1, wherein the prediction data includes a recommended body position of the living body when the intervention is performed.

4. The surgery support apparatus according to claim 1, further comprising
an input data generation unit that generates input data input to the first learned artificial intelligence algorithm using a second advance image acquired in advance for the living body to be treated.

5. The surgery support apparatus according to claim 4, wherein the input data generated by the input data generation unit is the same type of data as data used for learning of the first learned artificial intelligence algorithm.

6. The surgery support apparatus according to claim 4, wherein the input data generation unit generates, as the input data, a segment image obtained by dividing the second advance image into images of a plurality of regions.

7. The surgery support apparatus according to claim 4, wherein the input data generation unit uses a plurality of second advance images including the second advance image.

8. The surgery support apparatus according to claim 7, wherein the plurality of second advance images are images having different tissue contrasts or images captured with different modalities.

9. The surgery support apparatus according to claim 1, further comprising
a display control unit that causes a display apparatus to display the information related to the intervention position generated by the prediction data generation unit together with a second advance image acquired in advance for the living body to be treated.

10. The surgery support apparatus according to claim 9, wherein the display control unit causes the display apparatus to display an inclination of a line connecting a position of a center of gravity of the object and the intervention position with respect to a coordinate axis of the second advance image.

11. The surgery support apparatus according to claim 10, wherein the display control unit superimposes and displays the inclination as a straight line on the second advance image.

12. The surgery support apparatus according to claim 10, wherein the display control unit displays, as a display of the inclination, an image obtained by rotating the second advance image by an angle corresponding to the inclination together with the second advance image.

13. The surgery support apparatus according to claim 1, wherein the object is a brain, and the prediction data generated by the prediction data generation unit is any one of a region indicating a craniotomy position, a contour of the region, a figure schematically illustrating the region, and coordinates including a center position and a radius of the intervention position.

14. A surgical navigation system comprising:
the surgery support apparatus according to claim 1;
a display apparatus that displays a medical image; and
a position measuring apparatus that measures a position of a living body to be treated and a position of a surgical tool,
wherein the surgery support apparatus causes the display apparatus to display information related to an intervention position output by the prediction data generation unit and a position of the surgical tool measured by the position measuring apparatus.

* * * * *